US011731318B2

(12) United States Patent
Konishi et al.

(10) Patent No.: US 11,731,318 B2
(45) Date of Patent: Aug. 22, 2023

(54) METHOD FOR PRODUCING RECYCLED PRODUCT, RECYCLED RESIN PELLET, AND RECYCLED FILM

(71) Applicant: UNICHARM CORPORATION, Ehime (JP)

(72) Inventors: Takayoshi Konishi, Kagawa (JP); Toshio Hiraoka, Kagawa (JP); Noritomo Kameda, Kagawa (JP)

(73) Assignee: Unicharm Corporation, Ehime (JP)

( * ) Notice: Subject to any disclaimer, the term of this patent is extended or adjusted under 35 U.S.C. 154(b) by 977 days.

(21) Appl. No.: 16/566,291

(22) Filed: Sep. 10, 2019

(65) Prior Publication Data

US 2020/0001506 A1 Jan. 2, 2020

Related U.S. Application Data

(63) Continuation of application No. PCT/JP2017/045385, filed on Dec. 18, 2017.

(30) Foreign Application Priority Data

Mar. 31, 2017 (JP) .................................. 2017-071740

(51) Int. Cl.
*B29B 17/02* (2006.01)
*A61F 13/539* (2006.01)
(Continued)

(52) U.S. Cl.
CPC ............ *B29B 17/02* (2013.01); *A61F 13/539* (2013.01); *C08J 5/18* (2013.01);
(Continued)

(58) Field of Classification Search
CPC ............ B29B 17/02; B29B 2017/0231; B29B 2017/0293; A61F 13/539; A61F 2013/53908; C08J 5/18; C08J 2300/30
See application file for complete search history.

(56) References Cited

U.S. PATENT DOCUMENTS 5,322,225 A * 6/1994 Cina ........................ B03B 9/061
    241/38
7,306,697 B2 * 12/2007 Kikushima ............. B29B 17/02
    210/768

(Continued)

FOREIGN PATENT DOCUMENTS

EP    1415733 A1    5/2004
ES    2343725 A1    8/2010
(Continued)

OTHER PUBLICATIONS

International Search Report issued in corresponding International Application No. PCT/JP2017/045385 dated Jan. 23, 2018 (5 pages).

(Continued)

*Primary Examiner* — Michael McCullough
*Assistant Examiner* — Kalyanavenkateshware Kumar
(74) *Attorney, Agent, or Firm* — Osha Bergman Watanabe & Burton LLP (57) ABSTRACT

A method includes producing recycled products from a plurality of used absorbent articles, each including a top sheet, a back sheet and an absorbent body including absorbent body materials, by recovering a plurality of structural members from the plurality of used absorbent articles. At least one of the top sheet and the back sheet includes a film. The method includes: separating the plurality of used absorbent articles into a plurality of the films and the absorbent body materials; sorting the plurality of films into a plurality of types of recyclable films according to the filler contents of the plurality of films; and forming a plurality of types of recycled resin pellets from the plurality of types of recyclable films.

15 Claims, 5 Drawing Sheets

(51) Int. Cl.
 *C08J 5/18* (2006.01)
 *A61L 2/18* (2006.01)
 *A61L 11/00* (2006.01)

(52) U.S. Cl.
 CPC ....... *A61F 2013/53908* (2013.01); *A61L 2/18* (2013.01); *A61L 11/00* (2013.01); *B29B 2017/0231* (2013.01); *B29B 2017/0293* (2013.01); *C08J 2300/30* (2013.01)

(56) References Cited

U.S. PATENT DOCUMENTS

| | | | |
|---|---|---|---|
| 2014/0124128 A1* | 5/2014 | Moritz | B44C 1/14 428/335 |
| 2015/0298361 A1* | 10/2015 | Hayashi | B07B 15/00 241/47 |
| 2015/0376383 A1* | 12/2015 | Maldonado | A61F 13/551 604/372 |
| 2017/0305037 A1 | 10/2017 | Konishi et al. | |

FOREIGN PATENT DOCUMENTS

| | | |
|---|---|---|
| FR | 2922141 A1 | 4/2009 |
| JP | H08-183031 A | 7/1996 |
| JP | 2002-510238 A | 4/2002 |
| JP | 2002-273731 A | 9/2002 |
| JP | 2003-039023 A | 2/2003 |
| JP | 2003-200147 A | 7/2003 |
| JP | 2009-172599 A | 8/2009 |
| JP | 2013-173239 A | 9/2013 |
| JP | 2016-079525 A | 5/2016 |

OTHER PUBLICATIONS

Written Opinion of the International Searching Authority issued in corresponding International Application No. PCT/JP2017/045385 dated Jan. 23, 2018 (3 pages).

\* cited by examiner

“METHOD FOR PRODUCING RECYCLED PRODUCT, RECYCLED RESIN PELLET, AND RECYCLED FILM”

TECHNICAL FIELD

The present invention generally relates to methods of producing a recycled product from structural members of used absorbent articles, and to recycled resin pellets and recycled films.

BACKGROUND

Techniques for recycling absorbent articles such as used disposable diapers are known. Patent Literature 1, for example, discloses a method of producing recycled pulp from used sanitary products (absorbent articles). The method includes a step of applying physical force to used sanitary products in an acidic aqueous solution or the like to decompose the used sanitary products into pulp fibers and other materials (superabsorbent polymer, plastic materials, etc.), a step of separating the pulp fibers from the mixture of the pulp fibers and other materials, and a step of separating the plastic materials from the other materials. Plastic materials include nonwoven fabrics, plastic films, rubber and the like. The plastic materials can be treated to be RPF (Refuse Paper & Plastic Fuel), for example, and reused as solid fuel.
Patent Literature 1: Japanese Unexamined Patent Publication No. 2016-79525

In the method of Patent Literature 1, the pulp fibers recovered from used absorbent articles are regenerated into reusable recycled pulp. The plastic materials other than the pulp fibers, such as the nonwoven fabrics, plastic films and rubber, are treated together, as a mixture, without being separated into types. Thus, while the materials differ in composition and properties, it has been difficult to effectively utilize them in a way other than their bulk reutilization as solid fuel.

Furthermore, in the case of absorbent articles (sanitary products), even if the products are of the same type, such as the same type of paper diaper, the properties are often different for different nonwoven fabrics, plastic films or rubber components used in the absorbent articles depending on the manufacturer or on the purpose of use. For example, a plastic film used in a back sheet may contain or it may not contain fillers (inorganic fillers) used to provide air permeability, and even when fillers are present, the content of the fillers may be different. Generally, a higher filler content in a resin is, lower transparency of a film formed from the resin is, and easier formation of pores in the film is. Adjustment of the content of the filler in a resin is therefore very important when producing products using the resin. Even when plastic films have been successfully sorted out, since it is unknown whether the plastic films have fillers or how much the contents of the fillers in the plastic films, it is difficult to use the plastic films for purposes suited for their properties.

SUMMARY

One or more embodiments provide a method that can produce recycled products, when recycled products are to be produced from structural members of used absorbent articles each including a top sheet, a back sheet and absorbent body containing absorbent body material, with at least one of the top sheet and back sheet including a film as a structural member. The structural member can be sorted out and recovered according to its properties and reutilized according to its properties.

In one or more embodiments, a method of producing recycled products from a plurality of used absorbent articles each of which includes a top sheet, a back sheet and an absorbent body containing absorbent body materials, wherein at least one of the top sheet and the back sheet includes a film, by recovering a plurality of structural members from the plurality of used absorbent articles, the method including separating the plurality of used absorbent articles into a plurality of films and absorbent body materials, sorting the plurality of films into a plurality of types of recyclable films according to filler contents of the plurality of films, and forming a plurality of types of recycled resin pellets from the plurality of types of recyclable films.

In one or more embodiments, films are separated from used absorbent articles in the material-separating step, and the films are sorted out into a plurality of types of recyclable films according to their filler contents, in the film-sorting step. In the pellet-forming step of one or more embodiments, therefore, the plurality of types of recyclable films may be used to form a plurality of recycled resin pellets according to their filler contents. In other words, it is possible to obtain recycled resin pellets as a plurality of recycled products with a plurality of filler contents. Furthermore, not only are the filler contents of the recycled resin pellets known, but the materials are also known since they are formed from films that do not contain other plastic materials such as nonwoven fabrics or rubber. Therefore, when forming a recycled product using the recycled resin pellets, one or more suitable types of recycled resin pellets may be selected from among the plurality of recycled resin pellets with different filler contents, according to the properties of the recycled product that is to be formed. The selected recycled resin pellets may then be used, in combination with new resin pellets if necessary, to form a recycled product having the desired properties, such as a film that is usable as the back sheet of an absorbent article, or a film bag such as a trash bag (hereunder also referred to as "recycled film").

In other words, instead of merely extracting a plurality of films from a plurality of used absorbent articles, a plurality of recyclable films having a plurality of types of filler contents can be sorted out to form a plurality of types of recycled resin pellets of one or more embodiments. In addition, suitable types of recycled resin pellets can be selected out from among the plurality of types of recycled resin pellets, according to the properties of the recycled product that is to be formed, and utilized to allow production of recycled products. That is, when recycled products are to be produced from structural members of used absorbent articles, such as plastic films, the structural members may be sorted out and recovered according to their properties, and reutilized for production of recycled products, based on their compositions and properties.

The method of one or more embodiments may also be a method discussed above, wherein the sorting sorts the plurality of films into the plurality of types of recyclable films based on a difference in specific gravity between the plurality of films.

In one or more embodiments, a film that includes a large amount of filler (such as calcium carbonate) has a relatively high specific gravity, or in other words, films with different filler contents also have different specific gravities. In the film-sorting step of this method, therefore, the plurality of films is sorted out into the plurality of types of recyclable films based on the difference in specific gravity between the plurality of films. This allows structural members of used absorbent articles, such as plastic films, to be easily sorted out according to their properties.

The method of one or more embodiments may also be a method discussed above, wherein the sorting sorts the plurality of films into the plurality of types of recyclable films by a cyclone method.

In one or more embodiments, the plurality of films is sorted out by a cyclone method which utilizes a centrifugal separation process in a fluid such as air or water, thereby facilitating separation of the plurality of films into the plurality of types of recyclable films having different specific gravities, i.e. having different filler contents.

The method of one or more embodiments may further include selecting at least one type of recycled resin pellet from the plurality of types of recycled resin pellets based on one or more properties of a recycled film that is to be formed, and forming the recycled film using at least the selected type of recycled resin pellet.

In one or more embodiments, the recycled resin pellets formed by the pellet-forming step have known filler contents. In this method, therefore, recycled resin pellets having desired filler contents may be used in appropriate combinations as materials for the recycled film to be formed, according to the properties of the recycled film to be formed. Recycled films having desired properties can thus be formed.

The method of one or more embodiments may also be a method discussed above, wherein the film and the absorbent body materials are connected at joining sections by adhesive, and wherein in the separating of the plurality of used absorbent article, the adhesive at the joining sections is removed by dissolving the adhesive with a solvent.

In the material-separating step of one or more embodiments, the adhesive at the joining sections between a film (for example, a back sheet film) and another member (for example, a top sheet film or a nonwoven fabric or absorbent body materials) are removed with a solvent, thus allowing the film and the other member to be more easily separated from each other while maintaining their shapes. Thus, it is possible to more easily separate the structural members of the absorbent article according to their properties, so that they may be used for purposes suited for their properties.

When recycled resin pellets are used to form a recycled product of one or more embodiments, and the adhesive of the used absorbent articles is included in the recycled resin pellets, this can potentially prevent a quality recycled product from being formed. This method, however, allows films and other members to be separated without leaving the adhesive in the films, and therefore the purity of the films can be increased. In other words, it is possible to obtain a recyclable film containing no adhesive, and to thereby form recycled resin pellets containing no adhesive. The term "containing no adhesive" means that the adhesive residue is no greater than 1 mass % of the film.

Furthermore, since the adhesive in the film is removed, the weight of the film of one or more embodiments may be considered to be the weight of the film itself. It is therefore possible to properly sort out films by their difference in specific gravity.

The method of one or more embodiments may also be a method discussed above, wherein in the separating of the plurality of used absorbent articles, the plurality of films is heat-dried to remove the solvent.

In one or more embodiments, sterilization is extremely important for reutilization of structural members of used absorbent articles. In this method, the separated plurality of films is each subjected to heat drying, i.e. they are dried in a high-temperature atmosphere or with hot air, making it possible to not only vaporize off and remove the residual solvent on the surfaces of the films, but to also sterilize the films with the high-temperature atmosphere or hot air. This can help prevent a situation in which the solvent remains in the recyclable films, adversely affecting the recycled resin pellets and recycled product, while also helping to prevent a situation in which bacteria remain in the recyclable films and adversely affect the recycled resin pellets and recycled product. Furthermore, since the solvent in the film is removed, the weight of the film may be considered to be the weight of the film itself. It is therefore possible to properly sort out films by their difference in specific gravity.

The method of one or more embodiments may also be a method discussed above, wherein in the separating of the plurality of used absorbent articles, the plurality of used absorbent articles is swelled with water, the plurality of swelled used absorbent articles is disintegrated into the plurality of films and the absorbent body materials by applying a physical shock to the plurality of swelled used absorbent articles, and the plurality of films and the absorbent body materials are separated.

In the pretreatment step of this method of one or more embodiments, used absorbent articles are allowed to absorb water while in their original form without breakup, and also without inactivation of the superabsorbent polymers. Therefore, the used absorbent articles can be caused to absorb water up to nearly the maximum absorption of the used absorbent articles (for example, up to a maximum absorption of 80 mass % or greater). In other words, the used absorbent articles can be brought to a highly expanded state with water. A very high internal pressure is produced inside the used absorbent articles as a result. The internal pressure allows the used absorbent articles to be converted to a flat expanded state in water, from the rolled-up state or folded state after they have been disposed of (a used absorbent article is usually disposed of in a rolled-up state so that the excreta are not exposed on the front side and odor is minimized). Since the used absorbent articles are highly expanded at this time, some portions of the surfaces become prone to rupture. In the subsequent disintegration step, the used absorbent articles that have been expanded flat and have surfaces prone to rupture due to the expansion are subjected to physical shock, such as impact by a method of repeatedly raising them from their base sections and then dropping them down to cause impact onto their base sections. As a result, since further shock is applied to the used absorbent articles whose surfaces are prone to rupture, the surfaces rupture (detach) allowing the interior absorbent body materials of the used absorbent articles to effuse out (fly out) through the torn sections. This allows the used absorbent articles to disintegrate into at least the films and absorbent body materials. During this time, except for some partial cracking, the films maintain approximately the same shapes as when they were in the absorbent articles, or in other words, their original shapes. Compared to being broken up into fragments before disintegration, therefore, the sizes, shapes and masses of the films are distinctly different from the sizes, shapes and masses of the absorbent body materials, thus allowing the films to be easily separated from the absorbent body materials. Thus, structural members of the used absorbent articles can be separated from other structural members while maintaining their non-broken shapes, and the structural members can be used for purposes suited for their compositions and properties.

The method of one or more embodiments may also be a method discussed above, wherein the absorbent body materials include superabsorbent polymers and pulp fibers, and wherein in the separating of the plurality of used absorbent articles, the superabsorbent polymers are inactivated in an acidic aqueous solution, and the plurality of films is separated from a mixture containing the pulp fibers, the inactivated superabsorbent polymers, and any waste water discharged from the inactivation of the superabsorbent polymers.

In one or more embodiments, the superabsorbent polymers before inactivation are in a highly viscous state and cannot be considered to be easily separable from films. In this method, therefore, the superabsorbent polymers are inactivated before the films and absorbent body materials are separated, thus dewatering the superabsorbent polymers. Since this can lower the viscosity of the superabsorbent polymers, it is possible to easily separate the films from the superabsorbent polymers, and therefore from the mixture containing the pulp fibers. It is therefore possible to sort out the structural members of the absorbent articles according to their compositions and properties, so that they may be used for purposes suited for their properties.

The method of one or more embodiments may also be a method discussed above, wherein when the plurality of used absorbent articles is disintegrated, the plurality of swelled used absorbent articles is loaded into a horizontal-axis rotary drum, and the physical shock is applied to the plurality of swelled used absorbent articles by rotating the rotary drum, raising the plurality of swelled used absorbent articles from a lower area that is further downward in a vertical direction inside the rotary drum to an upper area that is further upward, and allowing the plurality of swelled used absorbent articles to fall by gravity from the upper area to the lower area and physically impact an inner wall of the rotary drum in the lower area.

In one or more embodiments, a horizontal-axis rotary drum that rotates around an imaginary rotation axis extending in the horizontal direction (for example, a rotary drum in the washing tank of a horizontal-axis washing machine) may be used to apply physical shock to the used absorbent articles. That is, the used absorbent articles set on the inner wall of the rotary drum are raised up from the lower area to the upper area in the rotary drum by rotation of the rotary drum and then fall down by gravity from the upper area to the lower area, impacting them with the inner wall of the lower area to allow shock to be applied to the used absorbent articles. By continuing rotation of the rotary drum, the shock of the impact can be stably, continuously and easily applied. This allows the joining sections between top sheets (nonwoven fabrics or films) and back sheets (films) of used absorbent articles to be stably torn (detached) and allows the used absorbent articles to be reliably disintegrated into films and absorbent body materials.

The method of one or more embodiments may also be a method discussed above, wherein in the swelling of the used absorbent article, the water is at a temperature between 70° C. to 98° C., and wherein each of the plurality of swelled used absorbent articles contains the water in an amount of 90 mass % or greater of a maximum absorption of each of the plurality of used absorbent articles.

In one or more embodiments, the water temperature is 70° C. or higher to allow the adhesive joining the films and other members to be softened by the heat of the water to lower the bonding force of the adhesive. Furthermore, limiting the water temperature to no higher than 98° C. can ensure that the water is present as a liquid, thus allowing the water to be reliably absorbed into the used absorbent articles. Furthermore, by allowing the used absorbent articles to absorb water in an amount of 90 mass % or greater of the maximum absorption of the used absorbent articles, it is possible to bring the used absorbent articles to their maximally expanded state. This can more reliably generate a state in which the surfaces are prone to rupture by expansion and can generate a state in which the bonding force of the adhesive is reduced. In the disintegration step, therefore, joining sections between the top sheets (nonwoven fabrics or films) and back sheets (films) which have reduced bonding force become torn (detached), allowing the absorbent body materials inside the used absorbent articles to effuse out (fly out) through the torn sections. This allows the used absorbent articles to more reliably disintegrate into at least the films and absorbent body materials. Sterilization is also extremely important for reutilization of used absorbent articles. By setting the water temperature to 70° C. or higher, an effect of sterilization (disinfection) can also be exhibited.

The method of one or more embodiments may also be a method discussed above, wherein the plurality of used absorbent articles are at least one selected from a group consisting of a paper diaper, a urine-absorbing pad, a sanitary napkin, a bed sheet and a pet sheet.

The method of one or more embodiments may be applied to used absorbent articles that are at least one of paper diapers, urine-absorbing pads, sanitary napkins, bed sheets and pet sheets.

A recycled resin pellet of one or more embodiments may be derived from films of absorbent articles having an adhesive residue of no greater than 1 mass %.

In one or more embodiments these recycled resin pellets are resin pellets from films obtained by recycling used absorbent articles, but the adhesive in the used absorbent articles is removed to an extremely low concentration of no greater than 1 mass % with respect to the recycled resin pellets. By using such recycled resin pellets, therefore, it is possible to form other recycled products of higher quality, such as plastic films or plastic bags of higher quality, compared to when the adhesive is present at high concentration.

A recycled film of one or more embodiments may be derived from films of absorbent articles having an adhesive residue of no greater than 1 mass %.

In one or more embodiments these recycled films are recycled films from films obtained by recycling used absorbent articles, but the adhesive in the used absorbent articles is removed to an extremely low concentration of no greater than 1 mass % with respect to the recycled films. Therefore, the recycled films may be considered to be recycled films of more excellent quality, including tensile strength and tensile elongation, compared to films containing an adhesive at high concentration. Incidentally, the recycled films can be formed using a mixture of the recycled resin pellets (of claim 12) having an adhesive residue of no greater than 1 mass %, obtained by recycling of used absorbent articles, together with virgin resin pellets (new resin pellets).

According to the method of one or more embodiments, it is possible to produce recycled products from structural members of used absorbent articles by sorting out and recover the structural members according to their properties and reutilizing them for production of the recycled products based on their properties.

DETAILED DESCRIPTION

Embodiments of the present invention will now be described. A "used absorbent article" is an absorbent article that has been used by a user, and usually it is an absorbent article in a state of having absorbed liquid excreta from the user. For one or more embodiments, however, used absorbent articles also include absorbent articles that have been used but have not absorbed excreta, as well as unused ones.

An example of the construction of an absorbent article of one or more embodiments will now be described. The absorbent article includes a top sheet, a back sheet and an absorbent body situated between the top sheet and back sheet. The absorbent article may be a paper diaper, a urine-absorbing pad, a sanitary napkin, a bed sheet or a pet sheet, for example. The top sheet, back sheet and absorbent body are formed of structural members such as nonwoven fabrics, films, pulp fibers and superabsorbent polymers, and they are joined together by an adhesive. An example of the size of an absorbent article is a length of about 15 to 100 cm and a width of 5 to 100 cm.

The structural member of the top sheet of one or more embodiments may be a nonwoven fabric or film, for example, and specifically this includes liquid-permeable nonwoven fabrics, synthetic resin films having liquid permeation holes, and composite sheets of the same. The structural member of the back sheet may also be a nonwoven fabric or film, for example, and specifically this includes liquid-impermeable nonwoven fabrics, liquid-impermeable synthetic resin films, and composite sheets of nonwoven fabrics and synthetic resin films. The materials of the nonwoven fabric or synthetic resin film are not particularly restricted so long as they can be used as absorbent articles, and examples include olefin-based resins such as polyethylene and polypropylene, polyamide-based resins such as 6-nylon and 6,6-nylon, and polyester-based resins such as polyethylene terephthalate (PET) and polybutylene terephthalate (PBT). The material of the nonwoven fabric or synthetic resin film may be polyethylene.

For one or more embodiments, at least one of the top sheet and back sheet of the absorbent article include a film as a structural member, but the following explanation will assume that the absorbent article has a film as the structural member of the back sheet and a nonwoven fabric as the structural member of the top sheet.

The back sheet of one or more embodiments may also include a gas-permeable outer sheet on the side opposite from the absorbent body in the thickness direction. The structural member used for the outer sheet may be the same type of structural member as the back sheet. The outer sheet is joined to the back sheet by an adhesive. The top sheet may also include a water-repellent side sheet on both outer sides in the widthwise direction. The structural member of each side sheet may be a water-repellent treated nonwoven fabric or gas-permeable synthetic resin film. The side sheet is joined to the top sheet by an adhesive. For one or more embodiments, when an outer sheet or side sheet is included in the absorbent article, the film may also include an outer sheet or side sheet.

When liquid permeability or gas-permeability is to be imparted to the film serving as the structural member, i.e. when the film is to be made porous, a filler (inorganic filler) may be added to the film. Pores are thus formed in the film by detachment occurring at the interface between the resin and filler of the film. The filler material is not particularly restricted so long as it can be used as an absorbent article, and examples include calcium carbonate, barium sulfate, calcium sulfate, barium carbonate, zinc oxide, magnesium oxide, titanium oxide, talc, silica, clay, kaolin, alumina, mica, and combinations of two or more of these.

The structural members of the absorbent body of one or more embodiments may be the absorbent body materials, i.e. pulp fibers and the superabsorbent polymers. Pulp fibers are not particularly restricted so long as they can be used in absorbent articles, and cellulosic fibers are an example. Examples of cellulosic fibers include wood pulp, crosslinked pulp, nonwood pulp, regenerated cellulose and semi-synthetic cellulose. The superabsorbent polymers (SAP) are not particularly restricted so long as they can be used in absorbent articles, and examples are polyacrylic acid salt-based, polysulfonic acid salt-based and maleic anhydride salt-based water-absorbent polymers.

One side and the other side of the absorbent body of one or more embodiments are joined to the top sheet and back sheet, respectively, via an adhesive. The portions (perimeter edge portions) of the top sheet that extend out from the absorbent body to surround the absorbent body, as viewed flat, are joined to the portions (perimeter edge portions) of the back sheet that extend out from the absorbent body to surround the absorbent body so as to surround the absorbent body, with an adhesive. The absorbent body is thus wrapped inside a joined structure between the top sheet and the back sheet. The adhesive is not particularly restricted so long as it can be used in absorbent articles and has its bonding force lowered when softened by warm water as described below, and an example is a hot-melt adhesive. Examples of hot-melt adhesives include rubber-mainly-based, such as styrene-ethylene-butadiene-styrene, styrene-butadiene-styrene and styrene-isoprene-styrene, or, olefin-mainly-based, such as polyethylene, pressure-sensitive adhesives or heat-sensitive adhesives.

The method of producing recycled products from structural members of used absorbent articles according to one or more embodiments will now be described in detail. For one or more embodiments, used absorbent articles are recovered, collected or acquired from an external source for reutilization (recycling). Also, for one or more embodiments, the individual used absorbent articles are recovered in a rolled-up state or folded state with the excreta-discharged top sheet on the inside, so that excreta are not exposed on the front side, and so that odor does not diffuse to the surroundings. The used absorbent articles do not need to be in a rolled-up state.

Figure 1:
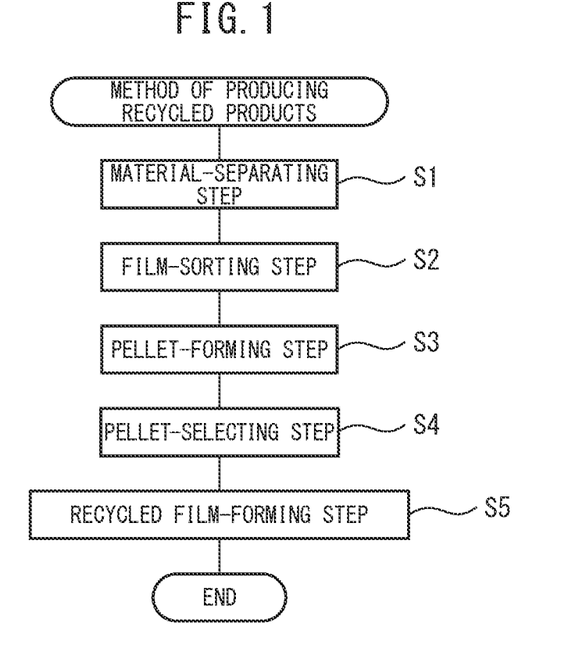
FIG. 1 is a flow chart showing a method of one or more embodiments.

FIG. 1 is a flow chart showing an example of the method of producing recycled products from structural members of used absorbent articles according to one or more embodiments. The method includes at least a material-separating step S1 of separating a plurality of used absorbent articles at least into a plurality of films and absorbent body materials, a film-sorting step S2 of sorting out the separated plurality of films into a plurality of types of recyclable films according to the filler contents of the separated plurality of films, and a pellet-forming step S3 of forming a plurality of types of recycled resin pellets by using the plurality of types of recyclable films that have been separated, according to their filler contents of the plurality of films. Each of the steps will now be explained.

Figure 2:
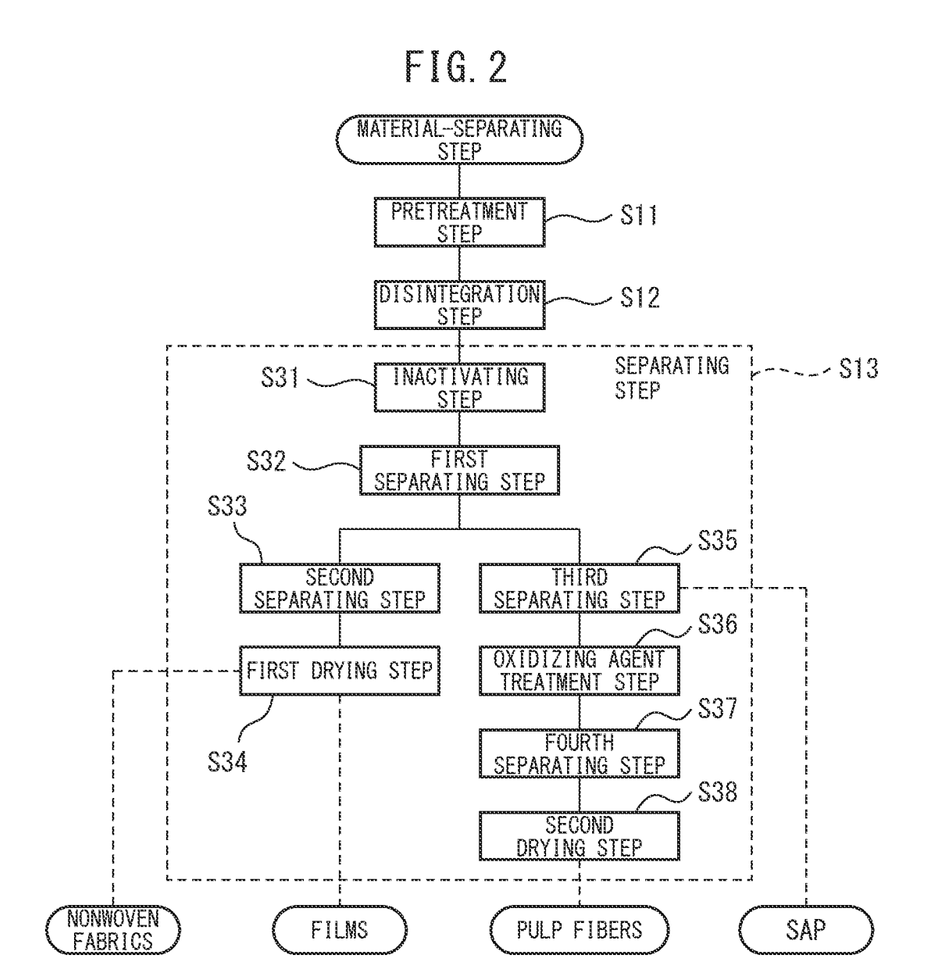
FIG. 2 is a flow chart illustrating a material-separating step of FIG. 1.

FIG. 2 is a flow chart illustrating the material-separating step of FIG. 1. The material-separating step S1 of one or more embodiments is a step in which a plurality of used absorbent articles are separated into at least a plurality of films and absorbent body materials, and for one or more embodiments, it is a step in which at least a plurality of films, a plurality of nonwoven fabrics and absorbent body materials are separated. The material-separating step S1 includes a pretreatment step S11 of swelling the plurality of used absorbent articles with water, a disintegration step S12 of applying physical shock to the swelled plurality of used absorbent articles to disintegrate the plurality of used absorbent articles into at least the plurality of films and the absorbent body materials, and a separating step S13 of separating the disintegrated plurality of films and the absorbent body materials.

In the pretreatment step S11 of one or more embodiments, the plurality of used absorbent articles are allowed to absorb water and swell while still in the state in which they were recovered from the external source, i.e. while without destruction or tearing and while still in any rolled-up or folded state (in other words, in their original form), and also without inactivation of the superabsorbent polymers of the absorbent body. For one or more embodiments, however, the used absorbent articles are either allowed to absorb warm water to swell, or after they have absorbed water and swelled the absorbed water is heated to produce warm water. Warm water is water at a higher temperature than ordinary temperature (20° C.±15° C. (5 to 35° C.: JIS Z 8703).

Usually, the amount of liquid excreta actually absorbed into a used absorbent article is much smaller than the maximum absorption amount of which the absorbent article is capable of absorbing (for example, the actual amount is about 10 to 20 mass % of the maximum absorption amount). For one or more embodiments, the used absorbent articles are immersed in warm water in the pretreatment step S11, and thus they are caused to absorb water up to nearly the maximum absorption amount of the used absorbent articles (for example, to 80 mass % or greater of the maximum absorption amount). Alternatively, the used absorbent articles are immersed in water at ordinary temperature to cause absorption of water up to nearly the maximum absorption amount of the used absorbent articles, and then the entire used absorbent articles are heated to the warm water temperature. This allows the used absorbent articles to be brought to a highly expanded state by the warm water or ordinary temperature water (hereunder also referred to simply as "warm water"). As a result, a very high internal pressure is produced inside the used absorbent articles. The purpose of using warm water as the water is primarily to weaken the adhesive force of the adhesive, as explained below.

Figure 3A:
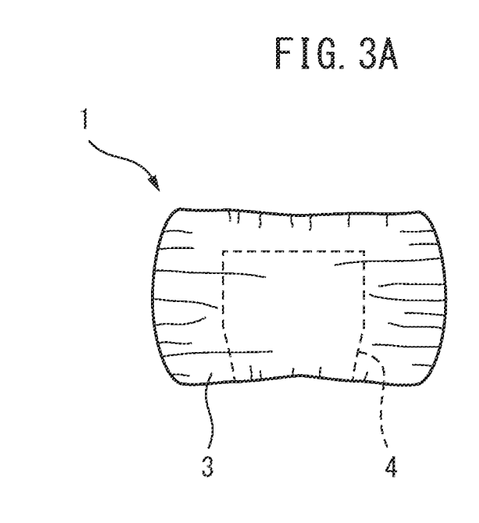
FIGS. 3A-B are schematic diagrams showing an example of a change of state of a used absorbent article in the pretreatment step of FIG. 2.
Figure 3B:
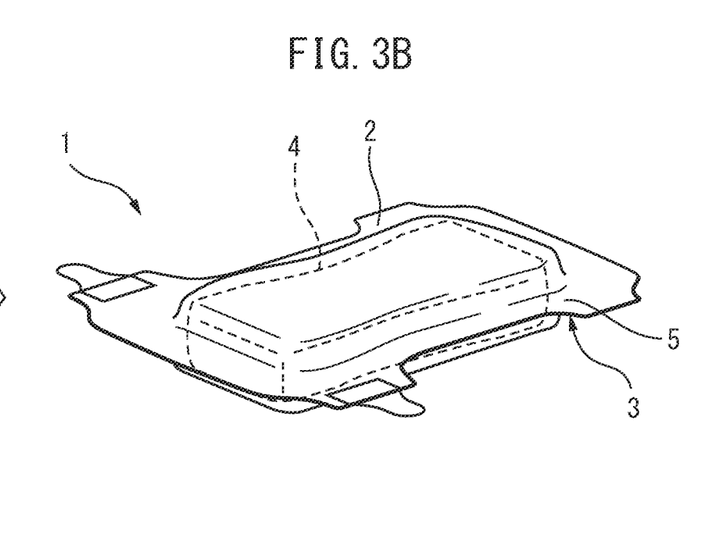

FIG. 3 is a schematic diagram showing an example of the change of state of a used absorbent article in the pretreatment step S11 of FIG. 2. FIG. 3A shows the state of the used absorbent article before immersion in warm water, and FIG. 3B shows the state after immersion in warm water. As shown in FIG. 3A, the used absorbent article 1 is initially in a rolled-up or folded state with the back sheet 3 on the outer side (hiding the top sheet 2 on the inner side). The used absorbent article 1 in this state is immersed in warm water, and thus the absorbent body 4 of the used absorbent article 1 absorbs warm water and expands in the warm water. The internal pressure of the used absorbent article 1 gradually increases as a result. The internal pressure produces a force which acts on the used absorbent article 1, causing it to open outward. As a result, as shown in FIG. 3B, the used absorbent article 1 in the rolled-up or folded state opens outward to an approximately flat state, exposing the top sheet 2. In other words, the used absorbent article 1 is brought to a flat expanded state in the warm water. Since the absorbent body 4 of the used absorbent article 1 is highly expanded at this time, having absorbed a large amount of warm water, it is highly prone to rupture at the surface, i.e. at locations on the top sheet 2 and back sheet 3 that are enveloping the absorbent body 4. In other words, the pretreatment step S11 of one or more embodiments causes the used absorbent article to be in a state where the surfaces are prone to tearing and rupture. Incidentally, if the used absorbent article 1 is initially in a flat expanded state, locations on the surface in that state will already be in a state that is highly prone to rupture. This state cannot be produced when the used absorbent article of Patent Literature 1, for example, has been broken up.

Moreover, when the used absorbent article of one or more embodiments is immersed in warm water and/or absorbs warm water, the adhesive (such as a hot-melt adhesive) used for joining between each of the structural members is softened by the heat of the warm water, thus lowering the bonding force of the adhesive. For example, the adhesive joining the perimeter edge portion of the top sheet with the perimeter edge portion of the back sheet can be softened by the heat of the warm water, thus lowering the bonding force of the adhesive. In addition, the adhesive joining the top sheet and the absorbent body and the adhesive joining the back sheet and the absorbent body can be softened by the heat of the warm water, thus lowering the bonding force of those adhesives.

In the pretreatment step S11 of one or more embodiments, as described above, expansion of the absorbent body of the used absorbent article can produce a state in which sections of the surface of the used absorbent article are prone to rupture, and a state with lower bonding force of the adhesive. If the used absorbent article is in such a state, the used absorbent article can be reliably disintegrated in the subsequent disintegration step.

The temperature of the warm water in the pretreatment step S11 is not particularly restricted so long as the adhesive in the used absorbent articles can be softened, and it may be 60° C. or higher, for example, and may be 70° C. to 98° C. In other words, the pretreatment step S11 includes a step of causing the used absorbent article to absorb warm water at 70° C. to 98° C., and swell. If the temperature of the warm water is 70° C. or higher, the adhesive joining the film (back sheet) and other members (nonwoven fabric of the top sheet or absorbent body material of the absorbent body) can be softened by the heat of the warm water, thus further lowering the bonding force of the adhesive. Limiting the warm water temperature to no higher than 98° C. can ensure that the warm water is present as a liquid, thus allowing the warm water to be more reliably absorbed into the used absorbent articles. Expansion of the absorbent body and heating with warm water can more reliably produce a state in which the surfaces of the used absorbent articles are prone to rupture, and a state with lower bonding force of the adhesive. The temperature of the warm water may be 75° C. to 90° C. The temperature of the warm water may be 75° C. to 85° C. Measurement of the temperature may be measurement of the warm water temperature when the used absorbent articles are immersed, or it may be measurement of the temperature within 5 mm inward from the surfaces of the used absorbent articles that have absorbed the water up to nearly their maximum absorption (by insertion of the tip of a temperature sensor).

In one or more embodiments, sterilization of structural materials is also extremely important for reutilization of used absorbent articles. The warm water temperature may be set to 70° C. or higher to allow an effect of sterilizing (disinfecting) the used absorbent articles to be exhibited.

The treatment time in the pretreatment step S11, i.e. the time for immersion of the used absorbent articles in the warm water, is not particularly restricted so long as the absorbent bodies of the used absorbent articles can expand, and it may be 2 to 60 minutes, for example, or 4 to 30 minutes. If the time is too short the absorbent bodies will not be able to expand sufficiently, and if the time is too long the treatment cost will be wastefully and unnecessarily increased.

The amount of warm water absorbed by the absorbent bodies in the pretreatment step S11 is not particularly restricted so long as the absorbent bodies can expand to a degree allowing the used absorbent articles to disintegrate in the subsequent disintegration step, but it may be, for example, 80 mass % or greater, and 90 mass % or greater, of the maximum absorption amount of the used absorbent articles. In other words, the pretreatment step S11 includes a step of causing the used absorbent articles to absorb warm water (water) in an amount of 90 mass % or greater of the maximum absorption amount of the used absorbent articles. This will allow the used absorbent articles to be brought to the maximally expanded state with the water. As a result, a very high internal pressure can be produced in the absorbent bodies of the used absorbent articles. If the used absorbent articles are in a folded state, the very high internal pressure allows the used absorbent articles to expand very easily into their flat states. At the same time, expansion of the absorbent bodies allows a rupture-prone state to be even more reliably produced at the surfaces of the used absorbent articles. As a result, the used absorbent articles can be more reliably disintegrated by physical shock applied to the used absorbent articles in the subsequent disintegration step.

The maximum absorption amount is measured by the following procedure.

(1) An unused absorbent article is dried in an atmosphere of 100° C. or higher and the mass of the absorbent article is measured.

(2) When a stretchable material, that can form a pocket so that water is less likely to reach the absorbent body (for example, a leg or waist stretching member), is disposed in the absorbent article, notches are formed in the stretching member to flatten the absorbent article.

(3) The absorbent article is immersed in a water bath filled with a sufficient amount of tap water, with the top sheet facing downward, and it is allowed to stand for 30 minutes.

(4) After standing, the absorbent article is placed on a net with the top sheet facing downward and drained for 20 minutes, after which the mass of the absorbent article is measured.

The difference in mass before and after immersion in the tap water is defined as the maximum absorption amount.

In addition, if all of the used absorbent articles are caused to absorb warm water up to approximately the maximum absorption of the used absorbent articles, then the weight per used absorbent article can be approximately the same for all of the used absorbent articles (if the used absorbent articles are of the same type). Therefore, the weight of all of the used absorbent articles may be divided by the weight per used absorbent article to estimate the total number of used absorbent articles collected, if the number was unknown when the disposable absorbent articles were collected. This allows the recovery amounts of each of the structural members to be estimated. For example, the number of films to be recovered and the amount of adhesive to be treated can be estimated from the total number of used absorbent articles that were collected. Therefore, the amount of treatment solution for treatment of each of the separate structural members in the steps following the pretreatment step S11 can be easily estimated, so that they can be easily prepared.

In the subsequent disintegration step S12 of one or more embodiments, physical shock is applied to the used absorbent articles that have expanded and swelled by the pretreatment step S11, thus disintegrating the used absorbent articles into at least a plurality of films (back sheets) and absorbent body materials (absorbent bodies). For one or more embodiments, the disintegration is into films (back sheets), nonwoven fabrics (top sheets) and absorbent body materials (absorbent bodies).

As a result of pretreatment step S11 of one or more embodiments, the used absorbent articles expand to become flat, with some sections of the surfaces becoming prone to rupture by the expansion, and for one or more embodiments, in particular, the bonding force of the adhesive is lowered by the heat of the warm water. In disintegration step S12, therefore, physical shock is applied to the used absorbent articles to cause locations on the surface to rupture, especially at the joining sections between the top sheets (nonwoven fabrics) and back sheets (films) where the bonding force has been lowered. This allows the joining sections to become torn (detached). The physical shock is not particularly restricted, and for example, it may be a method of beating the used absorbent articles onto a surface made of a harder material than the used absorbent articles, or a method of pressing the used absorbent articles from both sides while passing them between a pair of mutually facing rolls. Even if the water in which the used absorbent articles are immersed in the pretreatment step S11 is at ordinary temperature, the used absorbent articles can be caused to expand and the surfaces made prone to rupture, and even if the atmosphere in which shock is applied to the used absorbent articles in disintegration step S12 is at ordinary temperature, the used absorbent articles can be caused to rupture (tear) at locations on the surfaces.

Figure 4A:
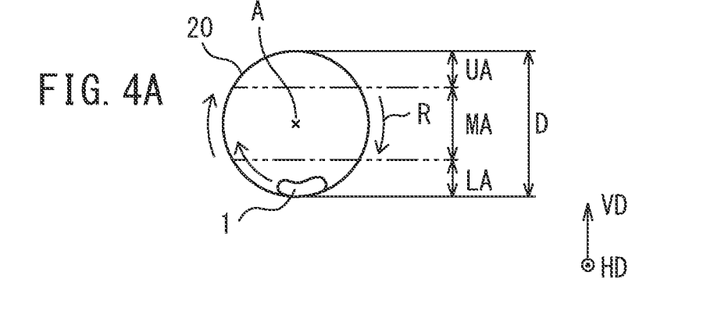
FIGS. 4A-C are schematic diagrams showing an example of a disintegration process in a disintegration step of FIG. 2.
Figure 4B:
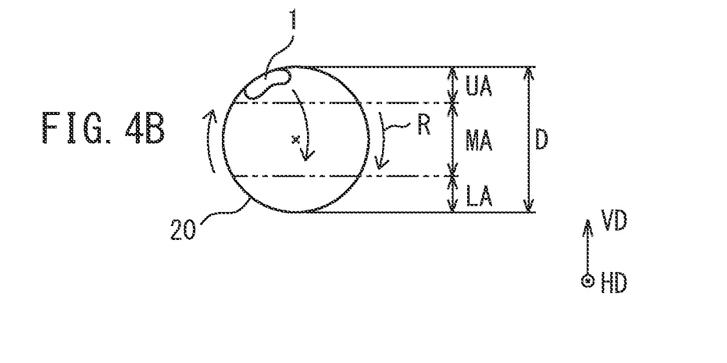
Figure 4C:
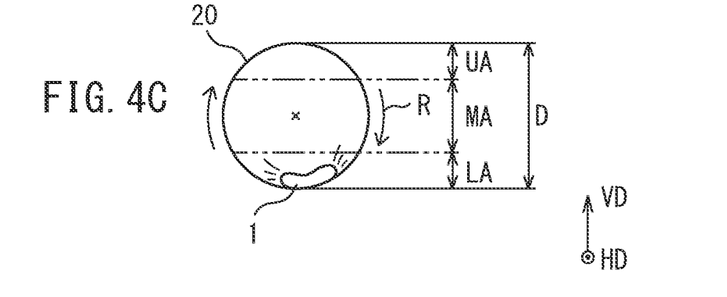

For one or more embodiments, the following method is employed as an example of a method of beating a used absorbent article on a surface made of a harder material than the used absorbent article. FIGS. 4A-C is a schematic diagram showing an example of the disintegration process in the disintegration step S12 of FIG. 2. FIGS. 4A-C show the method of applying physical shock to the used absorbent article 1. Specifically, disintegration step S12 includes a loading step of loading the swelled used absorbent article 1 into a rotary drum 20, and a shock step of applying physical shock to the used absorbent article 1 by rotation of the rotary drum 20.

As shown in FIG. 4A, the rotary drum 20 is a horizontal-axis rotary drum that rotates (R) around an imaginary rotation axis A extending in the horizontal direction HD. The rotary drum 20 may be a rotary drum in the washing tank of a horizontal-axis washing machine, for example, and therefore disintegration step S12 may be carried out using a horizontal-axis washing machine. The horizontal-axis washing machine used may be an ECO-22B by Inax Corp., for example. The rotary drum 20 has a lower area LA that is further downward and an upper area UA that is further upward, in the vertical direction VD, and a center area MA between the lower area LA and the upper area UA. The lower area LA is an area of D/3 and may be an area of the D/4 at the lower end in the vertical direction VD of the rotary drum 20, where D is the inner diameter of the rotary drum 20. The upper area UA is an area of D/3 and may be an area of the D/4 at the upper end in the vertical direction VD of the rotary drum 20. The inner diameter D and depth may be 50 to 150 cm and 30 to 120 cm, for example.

In the loading step, as shown in FIG. 4A, used absorbent articles 1 are set on the inner wall of the rotary drum 20 in the lower area LA. During this time, the total number of used absorbent articles 1 that are set is a number in an amount that allows sufficient shock to be applied to the used absorbent articles 1 in the shock step, and at maximum it is the number that fills the lower area LA. If the number is too large, movement of the used absorbent articles in the rotary drum 20 will be minimal, and it may not be possible to apply shock to the used absorbent articles.

In the subsequent shock step, as shown in FIG. 4B, the rotary drum 20 is rotated to lift the used absorbent articles 1 from the lower area LA to the upper area UA in the rotary drum 20. Then, as shown in FIG. 4C, the used absorbent articles 1 fall by gravity from the upper area UA to the lower area LA, thus impacting with the inner wall of the rotary drum 20 in the lower area LA. This step allows physical shock to be applied to the used absorbent articles 1.

The rotational speed of the rotary drum 20 is not particularly restricted so long as it allows the shock step to be carried out, and it may be 30 times/min to 100 times/min, for example. The temperature of the used absorbent articles 1 is also kept at a relatively high temperature by the warm water absorbed into the used absorbent articles 1, but the temperature of the atmosphere in the rotary drum 20 may be 70° C. or higher. The temperature of the atmosphere in the rotary drum 20 may be 75° C. or higher, from the viewpoint of minimizing reduction in the temperature of the adhesive and maintaining a sterilizing effect. The temperature in the rotary drum 20 may be no higher than 98° C. The temperature in the rotary drum 20 may be no higher than 90° C. from the viewpoint of handling the used absorbent articles 1. The amount of water in the rotary drum 20 may be as small as possible, and it is small enough so that at least the used absorbent articles 1 are not lower than the water surface in the shock step. If the used absorbent articles 1 are lower than the water surface, the shock to the used absorbent articles 1 will be absorbed by the water, making it difficult to apply the intended shock to the used absorbent articles 1.

The treatment time during the shock step, i.e. the time for rotation of the rotary drum 20, is not particularly restricted so long as the top sheets 2 and back sheets 3 and the absorbent body materials can be disintegrated, and it may be 2 to 40 minutes, for example, and may be 4 to 20 minutes.

Figure 5:
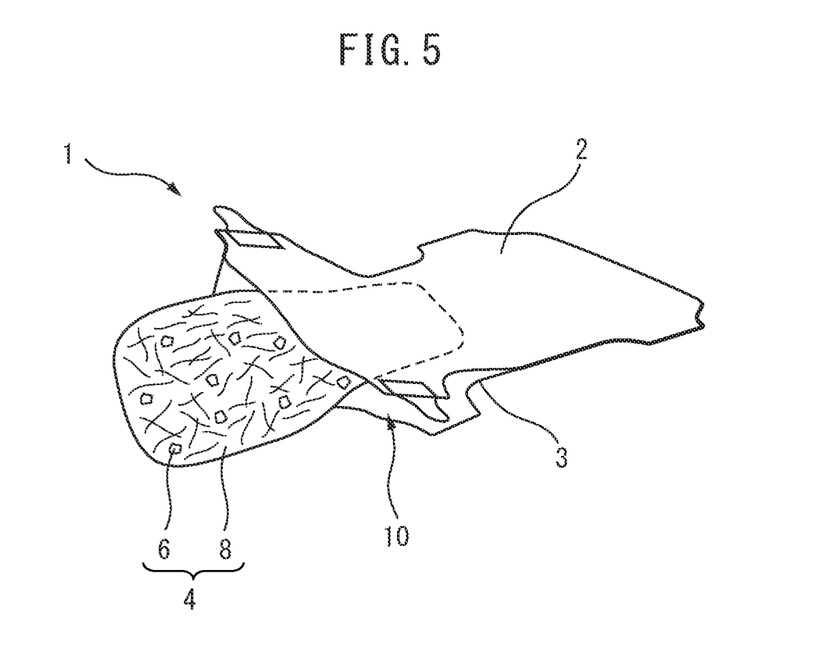
FIG. 5 is a schematic diagram showing an example of a used absorbent article that has disintegrated in the disintegration step of FIG. 2.

FIG. 5 is a schematic diagram showing an example of a used absorbent article 1 that has disintegrated in the disintegration step of FIG. 2. The joining section between the top sheet 2 (nonwoven fabric) and the back sheet 3 (film) of the used absorbent article 1 is ruptured and torn by the physical shock. At the same time, the absorbent body materials (pulp fiber 8 and water-absorbent polymer 6) of the used absorbent article 1 effuse out (fly out) through the torn section 10 by internal pressure of the absorbent body 4. This allows the used absorbent article 1 to disintegrate into the top sheet 2 (nonwoven fabric) and back sheet 3 (film) and the absorbent body materials (pulp fiber 8 and water-absorbent polymer 6).

In one or more embodiments, in particular, shock can be applied to the used absorbent article 1 by beating of the used absorbent article 1 by gravity from the upper area UA toward the lower area LA using the horizontal-axis rotary drum 20. By continuing rotation of the rotary drum 20 it is possible to easily apply such shock in a stable and continuous manner. This allows the joining section between the top sheet 2 (nonwoven fabric) and back sheet 3 (film) of the used absorbent article 1 to be more stably torn (detached), and allows the used absorbent article 1 to be reliably disintegrated into the film and the absorbent body material. An existing type of washing machine may be used.

Next, in separating step S13, the disintegrated plurality of films (back sheets) and absorbent body materials (pulp fibers and water-absorbent polymers) are separated. In one or more embodiments, the plurality of films (back sheets) and the plurality of nonwoven fabrics (top sheets) are separated from the absorbent body materials (pulp fibers and water-absorbent polymers). However, the nonwoven fabrics may also be joined to films. During this time, the back sheets (films) and top sheets (nonwoven fabrics) essentially maintain their original shapes, i.e. the same shapes as when they were in the absorbent articles. Compared to being broken up into fragments before disintegration, therefore, the sizes, shapes and masses of the top sheets (nonwoven fabrics) and back sheets (films) are distinctly different from the sizes and shapes of the absorbent body materials. In the separating step S13, therefore, the top sheets (nonwoven fabrics) and back sheets (films) can be easily separated from the absorbent body materials (pulp fibers and water-absorbent polymers). The separating method is not particularly restricted, and for example, it may be a method of using a screen through which the absorbent body materials pass but the top sheets and back sheets do not pass. This will allow the structural members such as films to be separated from the other structural members while maintaining their shapes without breaking up. The structural members, such as films, of the absorbent articles can therefore be efficiently recovered.

In one or more embodiments, the separating step S13 may include an inactivating step S31 of inactivating the superabsorbent polymers in an aqueous solution containing an inactivating agent before separating the films and absorbent body materials, and a first separating step S32 of separating the films from a mixture containing the pulp fibers, the inactivated superabsorbent polymers and waste water discharged from the superabsorbent polymers by inactivation.

In the inactivating step S31, prior to the first separating step S32, the top sheets (nonwoven fabrics), the back sheets (films) and the absorbent body materials (pulp fibers and superabsorbent polymers) are immersed in an aqueous solution containing an inactivating agent that can inactivate the superabsorbent polymers. This allows inactivation of the superabsorbent polymers adhering to the top sheets, the back sheets and the pulp fibers. It is thus possible to convert the superabsorbent polymers which were in a highly viscous state before inactivation, into superabsorbent polymers in a low-viscosity state, due to dewatering by inactivation.

The inactivating agent is not particularly restricted, and it may be an inorganic acid, an organic acid, lime, calcium chloride, magnesium sulfate, magnesium chloride, aluminum sulfate, aluminum chloride or the like. Inorganic acids and organic acids may be used among these because they do not leave residue of ash in the pulp fibers. When an inorganic acid or organic acid is used as the inactivating agent, the pH of the inorganic acid aqueous solution or organic acid aqueous solution is no higher than 2.5 and may be 1.3 to 2.4. The aqueous solution containing the inactivating agent may therefore be considered to be an acidic aqueous solution. If the pH is too high, it may not be possible to sufficiently lower the water-absorbing capacity of the superabsorbent polymers. The sterilizing power can also be potentially lowered. If the pH is too low there will be a risk of corrosion of the equipment, and large amounts of alkaline chemicals will be necessary for neutralizing treatment during waste water treatment. Examples of inorganic acids include sulfuric acid, hydrochloric acid and nitric acid. Sulfuric acid may be used from the viewpoint of cost and the absence of chlorine. Organic acids include citric acid, tartaric acid, glycolic acid, malic acid, succinic acid, acetic acid and ascorbic acid. Citric acid may be used. The chelating effect of citric acid traps metal ions and the like present in excreta, allowing their removal, and the washing effect of citric acid can potentially provide a high fouling component-removal effect. The pH will vary depending on the water temperature, where the pH in one or more embodiments may be the pH measured at an aqueous solution temperature of 20° C. The inorganic acid concentration of the inorganic acid aqueous solution is not particularly restricted so long as the pH of the inorganic acid aqueous solution is no higher than 2.5, but when the inorganic acid is sulfuric acid the sulfuric acid concentration may be 0.1 mass % to 0.5 mass %. The organic acid concentration of the organic acid aqueous solution is also not particularly restricted so long as the pH of the organic acid aqueous solution is no higher than 2.5, but when the organic acid is citric acid the citric acid concentration may be 2 mass % to 4 mass %.

The treatment temperature in the inactivating step S31, i.e. the temperature of the aqueous solution containing the inactivating agent, is not particularly restricted so long as the inactivation reaction proceeds. The treatment temperature may be room temperature or higher than room temperature, and it may be 15 to 30° C., for example. The treatment time in the inactivating step S31, i.e. the time for immersing the top sheets, back sheets and absorbent body materials in the aqueous solution containing the inactivating agent, is not particularly restricted so long as the superabsorbent polymers is inactivated and dewatered, and it may be 2 to 60 minutes, for example, and may be 5 to 30 minutes. The amount of aqueous solution in the inactivating step S31, i.e. the amount of the aqueous solution containing the inactivating agent, is not particularly restricted so long as the inactivation reaction proceeds. The amount of the aqueous solution may be 300 to 3000 parts by mass. The amount of the aqueous solution may be 500 to 2500 parts by mass. The amount of the aqueous solution may be 1000 to 2000 parts by mass with respect to 100 parts by mass of the used absorbent articles.

In the first separating step S32, the top sheets (nonwoven fabrics) and back sheets (films) are separated from the mixture containing the pulp fibers, the inactivated superabsorbent polymers and the waste water that has been discharged from the superabsorbent polymers by inactivation. The waste water is water released from the superabsorbent polymers by dewatering with the aqueous solution containing the inactivating agent in the inactivating step S31, or in other words, waste water that includes liquid from excreta and water from the warm water.

In one or more embodiments, the method of separating the top sheets and back sheets from the pulp fibers, superabsorbent polymers and waste water in the first separating step S32 is not particularly restricted. For example, the products of the inactivating step (top sheets, back sheets, pulp fibers, superabsorbent polymers, waste water, etc.) may be discharged while passing through a screen with a mesh opening of 5 to 100 mm and a mesh opening of 10 to 60 mm. This will allow the pulp fibers, superabsorbent polymers and waste water to be left in the drainage while the top sheets and back sheets remain on the screen, thereby separating them. Other large matter such as nonwoven fabrics and films may also remain on the screen. In particular, since the superabsorbent polymers are in a highly viscous state before inactivation, separation of the superabsorbent polymers adhering to the top sheets, back sheets and pulp fibers is by no means easy. After inactivation, however, the superabsorbent polymers are in a state of low viscosity due to the dewatering, and therefore the superabsorbent polymers adhering to the top sheets, back sheets and pulp fibers can be easily separated from the top sheets, back sheets and pulp fibers. Therefore, the structural members of the absorbent articles can be efficiently separated and recovered.

In one or more embodiments, the separating step S13 may further include a second separating step S33 of removing the adhesive at the joining sections between the films and other members by a solvent that dissolves the adhesive at the joining sections. In one or more embodiments, the adhesive at the joining sections between the films, nonwoven fabrics and absorbent body materials is removed by a solvent that dissolves the adhesive at the joining sections.

In the second separating step S33, the adhesive at the joining sections between the films (back sheets) and the other members (the nonwoven fabrics of the top sheets, and the absorbent body materials of the absorbent bodies remaining on the surfaces of the top sheets and back sheets) is removed by a solvent. This allows the films and other members to be separated from each other while maintaining their shapes without breaking up. The structural members, such as films, of the absorbent articles can therefore be efficiently recovered. Moreover, since the films and other members can be separated without leaving the adhesive in the films, the films can be reused as highly pure resins. This can minimize adverse effects of the adhesive when the films are reutilized. This description for films also applies to nonwoven fabrics.

The solvent to be used in the second separating step S33 is not particularly restricted so long as it can dissolve the adhesive, and examples include terpenes including at least one of terpene hydrocarbons, terpene aldehydes and terpene ketones. In this step, a terpene-containing aqueous solution is used, with the terpene concentration of the aqueous solution being between 0.05 mass % and 2 mass %, for example. The concentration may be 0.075 to 1 mass %. If the terpene concentration is too low, it may not be possible to dissolve the adhesive at the joining sections. Cost may increase if the terpene concentration is too high, on the other hand. The terpene not only dissolves the adhesive, such as a hot-melt adhesive, but also has a washing effect on contaminating oils. Therefore, when printing or the like is present on the structural members of the absorbent articles, such as their back sheets, the terpene can also decompose and remove the printing ink.

Terpene hydrocarbons include myrcene, limonene, pinene, camphor, sabinene, phellandrene, paracymene, ocimene, terpinene, carene, zingiberene, caryophyllene, bisabolene and cedrene. Limonene, pinene, terpinene and carene may be used among these. Examples of terpene aldehydes include citroneral, citral, cyclocitral, safranal, phellandral, perillaldehyde, geranial and neral. Examples of terpene ketones include camphor and thujone. Terpene hydrocarbons may be terpenes. For example, limonene may be used. Limonenes are of three types: d-limonene, l-limonene and dipentene (dl-limonene), and all of them are suitable for use. A single type of terpene may be used, or two or more may be used in combination.

The treatment temperature in the second separating step S33, i.e. the temperature of the aqueous solution containing the solvent, is not particularly restricted so long as dissolution of the adhesive proceeds to disintegrate the used absorbent articles into its structural members. The treatment temperature may be room temperature or higher than room temperature, and it may be 15 to 30° C., for example. The treatment time in the second separating step S33, i.e. the time for immersion of the top sheets, back sheets and absorbent body materials in the aqueous solution containing the solvent, is not particularly restricted so long as dissolution of the adhesive proceeds to disintegrate the used absorbent articles into its structural members. The treatment time may be 2 to 60 minutes, for example, and may be 5 to 30 minutes. The amount of aqueous solution in the second separating step S33, i.e. the amount of the aqueous solution containing the solvent, is not particularly restricted so long as dissolution of the adhesive proceeds to disintegrate the used absorbent articles into their structural members. The amount of the aqueous solution may be 300 to 3000 parts by mass. The amount of the aqueous solution may be 500 to 2500 parts by mass with respect to 100 parts by mass of the used absorbent articles. The amount of adhesive remaining on the films, nonwoven fabrics and absorbent body materials after the second separating step S33 can be limited to no greater than 1 mass % with respect to the films, nonwoven fabrics and absorbent body materials.

According to one or more embodiments, the second separating step S33 is carried out in tandem with the inactivating step S31. That is, the superabsorbent polymers adhering to the top sheets, back sheets and pulp fibers may be inactivated while dissolving the adhesive adhering to the top sheets, back sheets and pulp fibers. In this case, the aqueous solution used to immerse the top sheets, back sheets, pulp fibers and superabsorbent polymers may be an aqueous solution containing both the inactivating agent and the solvent. This will allow the back sheets (films), top sheets (nonwoven fabrics) and absorbent bodies (pulp fibers and superabsorbent polymers) to be in an essentially separated state in the aqueous solution during the inactivating step S31. In addition, it will allow separation of the back sheets (films), top sheets (nonwoven fabrics) and absorbent bodies (pulp fibers and superabsorbent polymers) in the subsequent first separating step S32, so that the second separating step S33 can be omitted. In this case, the back sheets (films) and top sheets (nonwoven fabrics) are essentially separated by removal of the adhesive.

In one or more embodiments, the separating step S13 may further include, after the step of removing the adhesive at the joining sections, a first drying step S34 of drying the films to remove the solvent by an atmosphere at higher temperature than room temperature, or by hot air. In one or more embodiments, the nonwoven fabrics are also dried in this step.

In one or more embodiments, sterilization is extremely important for reutilization of used absorbent articles. In the first drying step S34, a step of drying the separated films (back sheets) and nonwoven fabrics (top sheets) with a high-temperature atmosphere or hot air is carried out. The drying temperature may be 105 to 210° C., for example, and may be 110 to 190° C. The drying time will differ depending on the drying temperature, but it may be 10 to 120 minutes, for example, and may be 15 to 100 minutes. This will not only allow vaporizing removal of the residual solvent on the surfaces of the films and nonwoven fabrics, but will also allow sterilization of the films and nonwoven fabrics by the high-temperature atmosphere or hot air. The solvent can thus be removed while providing a sterilizing (disinfecting) effect.

The separating step S13 of may also include a third separating step S35 of separating the pulp fibers from the separated mixture, and an oxidizing agent treatment step S36 of treating the separated pulp fibers with an aqueous solution that includes an oxidizing agent, to reduce molecular weight of the residual superabsorbent polymers in the pulp fibers, thereby solubilizing and removing the residual superabsorbent polymers.

In one or more embodiments, the method of separating the pulp fibers from the separated mixture (including pulp fibers, superabsorbent polymers and waste water) in the third separating step S35 is not particularly restricted, and for example, the separated mixture may be discharged while passing through a screen with a mesh opening of 0.1 to 4 mm, and with a mesh opening of 0.15 to 2 mm. This will allow the superabsorbent polymers and waste water to be left in the drainage while the pulp fibers (residual superabsorbent polymers on the surfaces) remain on the screen, thereby separating the pulp fibers from the mixture. The pulp fibers include numerous impurities, but they can be reutilized depending on the purpose.

In the oxidizing agent treatment step S36, the inactivated superabsorbent polymers remaining on the surfaces of the separated pulp fibers are oxidatively decomposed with an oxidizing agent, thus being reduced in molecular weight and solubilized, and is removed from the surfaces of the pulp fibers. The oxidatively decomposed, molecular weight-reduced and solubilized state of the superabsorbent polymers means a state in which it passes through a 2 mm screen. This allows removal of the impurities such as superabsorbent polymers in the pulp fibers, to produce pulp fibers with a high level of purity. The oxidizing agent treatment can also accomplish secondary sterilization, bleaching and deodorization of the pulp fibers.

In one or more embodiments, the oxidizing agent is not particularly restricted so long as it can oxidatively decompose, reduce in molecular weight and solubilize the inactivated superabsorbent polymers, and examples include chlorine dioxide, ozone and sodium hypochlorite. Ozone may be used among these from the viewpoint of high decomposition performance and bleaching performance. When ozone is used as the oxidizing agent, the oxidizing agent treatment may be carried out by contacting the mixture containing the pulp fibers and superabsorbent polymers with the ozone, or more specifically, the ozone may be blown into the drainage containing the pulp fibers and the superabsorbent polymer. Ozone can be generated using, for example, an ozone water generator (such as an ED-OWX-2 ozone water exposure tester by EcoDesign, Inc. or an OS-25V ozone generator by Mitsubishi Electric Corp.).

In one or more embodiments, when ozone is to be blown into drainage containing the pulp fibers and superabsorbent polymers, the ozone concentration in the drainage is not particularly restricted so long as it is a concentration allowing decomposition of the superabsorbent polymers, and it may be 1 to 50 ppm by mass, for example, and may be 2 to 40 ppm by mass. If the concentration is too low it may not be possible to completely solubilize the superabsorbent polymers, potentially leading to residue of the superabsorbent polymers in the pulp fibers. If the concentration is too high, conversely, the oxidizing power will increase, potentially damaging the pulp fibers and possibly being more hazardous. The ozone treatment temperature is not particularly restricted so long as it is a temperature allowing decomposition of the superabsorbent polymers, and it may be room temperature, or higher than room temperature, for example. The ozone treatment time is also not particularly restricted so long as it is a time allowing decomposition of the superabsorbent polymers, and it may be 10 to 120 minutes, for example, and 20 to 100 minutes. The time may be short if the ozone concentration is high, but it must be a longer time if the ozone concentration is low. When ozone is to be blown into drainage containing the pulp fibers and inactivated superabsorbent polymers, the drainage may be acidic. For example, the pH of the drainage is no higher than 2.5. The pH of the drainage may be 1.5 to 2.4. Treatment in an acidic state can improve the superabsorbent polymer-decomposing and removal effect of the ozone, allowing the superabsorbent polymers to be decomposed in a shorter time.

In one or more embodiments, the separating step S13 may further include a fourth separating step S37 of separating the pulp fibers that have been treated with the oxidizing agent-containing aqueous solution from the oxidizing agent-containing aqueous solution, and a second drying step S38 of drying the separated pulp fibers.

In one or more embodiments, the method of separating the pulp fibers from the oxidizing agent-containing aqueous solution in the fourth separating step S37 is not particularly restricted, and it may be a method in which the treatment solution containing the pulp fibers is passed through a screen with a mesh opening of 0.15 to 2 mm, for example. If the treatment solution containing the pulp fibers is passed through a screen with a mesh opening of 0.15 to 2 mm, the drainage containing the product of oxidative decomposition of the superabsorbent polymers will pass through the screen while the pulp fibers will remain on the screen.

In the subsequent second drying step S38, the oxidizing agent-containing aqueous solution is treated, and the separated pulp fibers are dried with a high-temperature atmosphere or hot air. The drying temperature may be 105 to 210° C., for example, and may be 110 to 190° C. The drying time will differ depending on the drying temperature, but it may be 10 to 120 minutes, for example, and may be 15 to 100 minutes. This will allow the residual solvent on the surfaces of the pulp fibers to be vaporized and removed, so that highly pure pulp fibers with a very low superabsorbent polymers mixing ratio can be recovered. The structural members of the absorbent articles can therefore be efficiently recovered. The pulp fibers can also be sterilized (disinfected) by the high-temperature atmosphere or hot air.

Incidentally, the superabsorbent polymers may be recovered from the drainage containing the superabsorbent polymers and waste water separated by the third separating step S35. The recovering method is not particularly restricted and may be a method using a screen, for example, while the method of restoring the water-absorbing capacity of the recovered water-absorbent polymers may be a method of treatment with an aqueous alkali metal salt solution, for example. The residual drainage (with ozone dissolved in a trace amount of 10 ppm), which has been separated by the fourth separating step S37, may be circulated back to the pretreatment step S11. This allows the ozone-containing drainage to be used in a non-wasteful manner, and allows the pretreatment in the pretreatment step S11 and sterilization with the ozone to be carried out simultaneously.

In one or more embodiments, the film-sorting step S2 is carried out after the material-separating step S1. In the film-sorting step S2, the plurality of separated films is sorted out into a plurality of types of recyclable films according to their filler contents. For one or more embodiments, the separated back sheets (films) are sorted out into a plurality of types of recyclable films according to their filler contents.

In one or more embodiments, the plurality of separated films obtained in the material-separating step S1 have different filler (inorganic filler) contents. Films containing no filler are considered to be films with a filler content of zero (0). When films are to be newly formed, however, the properties such as moldability of the resin pellets for molding into film forms, or the stretchability for stretching of the films, will vary depending on the filler contents of the resin pellets that are used as the materials for the films. The properties such as the moisture permeability, gas permeability, strength and transparency of the obtained films will vary correspondingly. Therefore, when resin pellets are regenerated from different separated films and the regenerated resin pellets (hereunder also referred to as "recycled resin pellets") are to be used to form new recycled products, it is necessary for the filler contents of the recycled resin pellets to be determined beforehand. In one or more embodiments, recycled resin pellets are formed from separated films with known filler contents, without including nonwoven fabrics or absorbent body materials.

Specifically, the plurality of separated films that are to serve as the starting material for formation of the recycled resin pellets are sorted out into a plurality of types of recyclable films with different filler contents. For example, a plurality of films is sorted out into a plurality of groups (types) having specified filler contents. The groups (types) may be, for example, a group with a filler content of 0 mass %, a group with a filler content of greater than 0 mass % and less than 20 mass %, a group with a filler content of 20 mass % or greater and less than 40 mass %, a group with a filler content of 40 mass % or greater and less than 60 mass %, and a group with a filler content of 60 mass % or greater. However, there is no limitation to the number of groups and the ranges of their filler contents. The amount of adhesive remaining in each separated recyclable film is no greater than 1 mass % of the recyclable film.

In one or more embodiments, the method of sorting is not particularly restricted, but it is a method including a step of sorting out the plurality of films into a plurality of types of recyclable films based on the difference in specific gravity between the plurality of films. This is because a film that includes a large amount of filler has a relatively high specific gravity, or in other words, films with different filler contents also have different specific gravities. When the film is polyethylene and the filler is calcium carbonate, for example, the specific gravity is about 0.9 with a filler content of 0 mass %, while the specific gravity is about 1.4 with a filler content of 40 to 60 mass %. By thus sorting out the plurality of films into a plurality of types of recyclable films based on the difference in specific gravity between the plurality of films, it is possible to sort out the structural members of the used absorbent articles, such as plastic films, according to their properties.

In one or more embodiments, the step of sorting out the plurality of films into a plurality of types of recyclable films based on the difference in specific gravity between the plurality of films, in the film-sorting step S2, employs a cyclone method utilizing a centrifugal separation process in a fluid such as air or water. The apparatus used for the cyclone method may be an ACO Jet Separator CFS500-CFS1200 by Aco Co. By sorting out films using a cyclone method, it is possible to facilitate separation of a plurality of films into a plurality of types of recyclable films having different specific gravities, i.e. having different filler contents.

In one or more embodiments, the pellet-forming step S3 is carried out next. In the pellet-forming step S3, the plurality of types of recyclable films that have been separated are used to form a plurality of types of recycled resin pellets according to their filler contents.

For example, a plurality of recycled resin pellets is formed having filler contents suited for a plurality of types of recyclable films. Specifically, recycled resin pellets having filler contents of 0 mass %, and of 40 mass % or greater and less than 60 mass %, for example, are formed using recyclable films with filler contents of 0 mass %, and 40 mass % or greater and less than 60 mass %, respectively. Alternatively, a plurality of types of recyclable films may be combined in appropriate ways to form a plurality of recycled resin pellets with different filler contents. Specifically, recycled resin pellets having filler contents of 20 mass % to 30 mass % are formed using equal amounts of recyclable films having filler contents of 0 mass %, and 40 mass % or greater and less than 60 mass %, for example.

In one or more embodiments, the step of using recyclable films to form recycled resin pellets (pelletizing) in pellet-forming step S3 may be a method of melting the recyclable film starting material into a molten resin and extruding the molten resin from an extruder into a sheet or strand form while cutting it to an appropriate size. The pelletizing apparatus may be an HEM-type 75 mm vent-type extruder (strand cutting type) by On Machinery Co., Ltd. In the pellet-forming step, therefore, the plurality of types of recyclable films may be used to form recycled resin pellets according to their filler contents.

Since the amount of adhesive remaining in the recyclable film starting material is no greater than 1 mass %, the adhesive residue in the formed recycled resin pellets is also no greater than 1 mass % with respect to the recycled resin pellets. That is, this method can form recycled resin pellets from absorbent article films having an adhesive residue of no greater than 1 mass %. Since the plurality of types of recycled resin pellets are formed from used absorbent articles and can also be treated as products, they may also be considered to be recycled products.

In one or more embodiments, the recycled resin pellets that are formed in this manner are resin pellets obtained by recycling used absorbent articles, but with the adhesive removed to an extremely low concentration of no greater than 1 mass % with respect to the recycled resin pellets. By using such recycled resin pellets, therefore, it is possible to form other recycled products of higher quality, such as plastic films or vinyl or other plastic bags of higher quality, compared to when the adhesive is present at high concentration.

In one or more embodiments, a pellet-selecting step S4 and a recycled film-forming step S5 are also carried out. In the pellet-selecting step S4, at least one type of recycled resin pellets is selected from the plurality of types of recycled resin pellets, based on the properties of a recycled film that is to be formed. In the recycled film-forming step S5, at least one type of recycled resin pellets that were selected are used to form the recycled film.

The recycled resin pellets formed by the pellet-forming step S3 have known filler contents. In the pellet-selecting step S4, therefore, recycled resin pellets having desired filler contents are selected as material for the recycled film to be formed, according to the properties of the recycled film to be formed. Specifically, when a recycled film with a filler content of 20 to 30 mass % is to be formed, for example, recycled resin pellets having a filler content of 0 mass % and 40 to 60 mass % are selected in a mass ratio of 1:1. Alternatively, when a recycled film with a filler content of 5 to 10 mass % is to be formed, for example, recycled resin pellets having filler contents of 0 mass %, and 40 mass % or greater and less than 60 mass % are selected in a mass ratio of 7:1. Some of the recycled resin pellets may also be replaced with virgin resin pellets (non-recycled new resin pellets). The types of selected recycled resin pellets and virgin resin pellets are not limited to two types and may also be three or more types, so long as they include at least one type of recycled resin pellets.

The recycled resin pellets selected in the pellet-selecting step S4 may be loaded into a recycled film-forming apparatus in the recycled film-forming step S5 to form a recycled film having the desired properties. Specifically, recycled resin pellets having filler contents of 0 mass %, and 40 to 60 mass %, selected in a mass ratio of 1:1, for example, may be used to form a recycled film having a filler content of 20 to 30 mass %. Alternatively, recycled resin pellets having filler contents of 0%, and 40 mass % or greater and up to 60 mass %, selected in a mass ratio of 7:1, for example, may be used to form a recycled film having a filler content of 5 to 10 mass %. The recycled film is a film-like recycled product that can be formed from recycled resin pellets, and it may be a film that can be used as the back sheet of an absorbent article, or a trash bag or film-like bag, for example.

In one or more embodiments, the step of forming a recycled film using recycled resin pellets in the recycled film-forming step S5 may be a method of melting the recycled resin pellet starting material into a molten resin, and extruding the molten resin from the T-die of an extruder into a sheet form (T-die molding). Alternatively, it may be a method of extruding the molten resin into a cylindrical form from the inflation die of an extruder, and streaming air into the cylinder to inflate it (inflation molding). The T-die molding apparatus may be a biaxial-stretched film producing apparatus by Seika Corp. The inflation molding apparatus may be a multilayer inflation molding machine by Placo Co., Ltd. In the recycled film-forming step, therefore, the plurality of types of recycled resin pellets may be used to form recycled films according to their filler contents.

Since the amount of adhesive remaining in the recycled resin pellet starting material of one or more embodiments is no greater than 1 mass %, the adhesive residue in the formed recycled film is also no greater than 1 mass % with respect to the recycled film. That is, this method can form a recycled film from absorbent articles having an adhesive residue of no greater than 1 mass %.

In one or more embodiments, the recycled film that is formed in this manner is a recycled film obtained by recycling used absorbent articles, but with the adhesive removed to an extremely low concentration of no greater than 1 mass % with respect to the recycled film. Therefore, the recycled films may be considered to be recycled films of more excellent quality, including tensile strength and tensile elongation, compared to films containing adhesive at high concentration.

In one or more embodiments, films are separated from used absorbent articles in the material-separating step S1, and the films are sorted out into a plurality of types of recyclable films according to their filler contents, in the film-sorting step S2. In the pellet-forming step S3, therefore, the plurality of types of recyclable films may be used to form a plurality of recycled resin pellets according to their filler contents. In other words, it is possible to obtain recycled resin pellets as a plurality of recycled products with different filler contents. Furthermore, not only are the filler contents of the recycled resin pellets known, but the materials are also known since they are formed from films that do not contain other plastic materials such as nonwoven fabrics or rubber. Therefore, when forming a recycled product using resin pellets, one or more suitable types of recycled resin pellets may be selected from among the plurality of recycled resin pellets with different filler contents, according to the properties of the recycled product that is to be formed (pellet-selecting step S4). The selected recycled resin pellets may then be used, in combination with virgin resin pellets if necessary, to form a recycled product having the desired properties (for example, a recycled film as a film to be used as the back sheet of an absorbent article, or a bag such as a trash bag or plastic bag).

In other words, instead of merely extracting a plurality of films from a plurality of used absorbent articles, a plurality of recyclable films having a plurality of filler contents may be sorted out to form a plurality of types of recycled resin pellets. In addition, suitable types of recycled resin pellets may be selected out from among the plurality of types of recycled resin pellets, according to the properties of the recycled product that is to be formed, and utilized to allow production of recycled products. That is, when recycled products are to be produced from structural members of used absorbent articles, such as plastic films, the structural members may be sorted out and recovered according to their properties, and reutilized for production of recycled products, based on their properties.

In one or more embodiments, a recycled film such as a film to be used as a back sheet of an absorbent article, or as a trash bag or a film-like bag, is formed using recycled resin pellets, but the recycled product is not limited to such a recycled film. The resin pellets (recycled resin pellets) may also be used to form resin products other than recycled films, as recycled products, by methods such as extrusion molding or blow molding.

According to one or more embodiments, the material-separating step S1 may additionally have a pretreatment step S11 in which the used absorbent articles are in their original state without breakup and in a highly expanded state with water, without inactivation of the superabsorbent polymers. This can produce extremely high internal pressure in the used absorbent articles, so that some of the locations on the surfaces are in a state prone to rupture. Furthermore, by applying physical shock to the used absorbent articles that are in this state in the disintegration step S12, some of the locations on the surfaces can be torn, allowing the absorbent body materials inside them to effuse outward. This allows the used absorbent articles to disintegrate into at least the films (back sheets) and absorbent body materials. Since the films essentially maintain their original shapes during this time, they can be easily separated from the absorbent body materials in the subsequent separating step S13. This will allow the structural members such as films to be separated from the other structural members while maintaining their shapes without breaking up. The structural members, such as films, of the absorbent articles can therefore be efficiently recovered.

According to one or more embodiments, a terpene is used to remove the adhesive, thereby allowing a hot-melt adhesive bonding the structural members of the absorbent article to be dissolved at ordinary temperature. The absorbent articles can therefore be easily and cleanly dispersed, the pulp fibers and superabsorbent polymers can be separated from the absorbent articles, and the nonwoven fabrics and films can be separated while retaining the forms of each of the separate members. That is, it is possible to easily recover pulp fibers, films and nonwoven fabrics separately, without crushing the absorbent articles and without a complex separating step. When limonene is used as the terpene, a secondary effect of the limonene provides a refreshing, citrus-like odor and can therefore mask odors from excreta to some extent, reducing the burden of odors on operating personnel and the effect of odors on the surroundings. Since limonene is a monoterpene and has a structure similar to styrene, it can dissolve styrene-based hot-melt adhesives that are commonly used in absorbent articles. Since washing treatment of absorbent articles is possible at ordinary temperature, energy costs can be reduced and diffusion of odors can be minimized. Terpenes have a high washing effect for contaminating oils, and in addition to its dissolving effect for the hot-melt adhesive, it can also decompose and remove printing inks that may be present in printed matter on films, and therefore also allows recovery of printed films as highly pure plastic materials.

In one or more embodiments, if an organic acid aqueous solution with a pH of no higher than 2.5 has been used for inactivation of the superabsorbent polymers, the pulp fibers are unlikely to suffer degradation. When citric acid is used as the organic acid, the chelating effect and washing power of the citric acid can potentially provide an effect of removing fouling components from excreta. A sterilizing effect and a deodorant effect against alkaline odors may also be expected.

Furthermore, by decomposing and removing the superabsorbent polymers with an oxidizing agent, it is possible to prevent contamination of the pulp fibers or drastic increase in waste water due to water absorption by the superabsorbent polymers. By adjusting the type and concentration of oxidizing agent used, it is possible to simultaneously carry out oxidative decomposition and sterilization of the superabsorbent polymers. When an oxidizing agent treatment step is not provided, or ozone is used as the oxidizing agent in the oxidizing agent treatment step, absolutely no chlorine-based agents are used and therefore high-quality RPF can be produced from the recovered plastic members while avoiding damage to the furnace. If films are separated and recovered by the embodiment described above, they can be reused as recycled film starting materials for trash bags and the like. Since no salts are used during the treatment steps, there is no residue in the pulp fibers and high-quality pulp with a low ash content can be recovered.

As described above, in one or more embodiments, a film is used as the structural member of the back sheet and a nonwoven fabric is used as the structural member of the top sheet. However, one or more embodiments where a nonwoven fabric is the structural member of the back sheet and a film is the structural member of the top sheet, or where films are the structural members of both the back sheet and the top sheet, may also be carried out by the same method as the embodiments described above, and can exhibit the same function and effect. Moreover, a nonwoven fabric may likewise be used to form recycled resin pellets by the pellet-forming step S3 after the first drying step S34, in the same manner as a film containing no filler. A recycled product can then be formed using the recycled resin pellets from the nonwoven fabric. In addition, the amount of residual adhesive in the recycled resin pellets or recycled products can be reduced to no greater than 1 mass % with respect to the recycled resin pellets and recycled products, respectively, and therefore high quality can be achieved.

Although the disclosure has been described with respect to only a limited number of embodiments, those skilled in the art, having benefit of this disclosure, will appreciate that various other embodiments may be devised without departing from the scope of the present invention. Accordingly, the scope of the invention should be limited only by the attached claims.

S1 Material-separating step
S2 Film-sorting step
S3 Pellet-forming step

What is claimed is:

1. A method of producing recycled products from a plurality of used absorbent articles by recovering a plurality of structural members from the plurality of used absorbent articles, wherein each of the plurality of used absorbent articles comprises a top sheet, a back sheet, and an absorbent body comprising absorbent body materials, and wherein at least one of the top sheet and the back sheet comprises a film, the method comprising:
    separating the plurality of used absorbent articles into a plurality of the films and the absorbent body materials;
    sorting the plurality of films into a plurality of types of recyclable films according to filler contents of the plurality of films; and
    forming a plurality of types of recycled resin pellets from the plurality of types of recyclable films.

2. The method according to claim 1, wherein the plurality of films is sorted into the plurality of types of recyclable films based on a difference in specific gravity between the plurality of films.

3. The method according to claim 2, wherein the plurality of films is sorted into the plurality of types of recyclable films by a cyclone method.

4. The method according to claim 3, further comprising:
    selecting at least one type of recycled resin pellet from among the plurality of types of recycled resin pellets based on one or more properties of a recycled film that is to be formed, and
    forming the recycled film using at least the selected type of recycled resin pellet.

5. The method according to claim 2, further comprising:
    selecting at least one type of recycled resin pellet from among the plurality of types of recycled resin pellets based on one or more properties of a recycled film that is to be formed; and
    forming the recycled film using at least the selected type of recycled resin pellet.

6. The method according to claim 2, wherein the film and the absorbent body materials are connected at joining sections by an adhesive, and
    wherein in the separating of the plurality of used absorbent articles, the adhesive at the joining sections is removed by dissolving the adhesive with a solvent.

7. The method according to claim 6, wherein in the separating of the plurality of used absorbent articles, the plurality of films is heat-dried to remove the solvent.

8. The method according to claim 1, further comprising:
    selecting at least one type of recycled resin pellet from the plurality of types of recycled resin pellets based on one or more properties of a recycled film that is to be formed; and
    forming the recycled film using at least the selected type of recycled resin pellet.

9. The method according to claim 1, wherein the film and the absorbent body materials are connected at joining sections by an adhesive, and
    wherein in the separating of the plurality of used absorbent articles, the adhesive at the joining sections is removed by dissolving the adhesive with a solvent.

10. The method according to claim 9, wherein in the separating of the plurality of used absorbent articles, the plurality of films is heat-dried to remove the solvent.

11. The method according to claim 1, wherein in the separating of the plurality of used absorbent articles,
    the plurality of used absorbent articles is swelled with water,
    the plurality of swelled used absorbent articles is disintegrated into the plurality of films and the absorbent body materials by applying a physical shock to the plurality of swelled used absorbent articles, and
    the plurality of films and the absorbent body materials are separated.

12. The method according to claim 11, wherein the absorbent body materials include superabsorbent polymers and pulp fibers, and
    wherein in the separating of the plurality of used absorbent articles, the superabsorbent polymers are inactivated in an acidic aqueous solution, and
    wherein in the separating of the plurality of used absorbent articles, the plurality of films is separated from a mixture containing the pulp fibers, the inactivated superabsorbent polymers, and any waste water discharged from the inactivation of the superabsorbent polymers.

13. The method according to claim 11, wherein when the plurality of used absorbent articles is disintegrated,
    the plurality of swelled used absorbent articles is loaded into a horizontal-axis rotary drum, and
    the physical shock is applied to the plurality of swelled used absorbent articles by rotating the rotary drum, raising the plurality of swelled used absorbent articles from a lower area that is further downward in a vertical direction inside the rotary drum to an upper area that is further upward, and allowing the plurality of swelled used absorbent articles to fall by gravity from the upper area to the lower area and physically impact an inner wall of the rotary drum in the lower area.

14. The method according to claim 11, wherein in the swelling of the used absorbent article, the water is at a temperature between 70° C. to 98° C., and
    wherein each of the plurality of swelled used absorbent articles contains the water in an amount of 90 mass % or greater of a maximum absorption of each of the plurality of used absorbent articles.

15. The method according to claim 1, wherein the plurality of used absorbent articles are at least one selected from a group consisting of a paper diaper, a urine-absorbing pad, a sanitary napkin, a bed sheet and a pet sheet.

* * * * *